United States Patent [19]

Coffee et al.

[11] 4,316,914

[45] Feb. 23, 1982

[54] ELECTROSTATICALLY SPRAYABLE INSECTICIDAL FORMULATIONS

[75] Inventors: Ronald A. Coffee, Haslemere; Brian W. Young, Emmer Green; Michael R. Middleton, Arborfield Cross, all of England

[73] Assignee: Imperial Chemical Industries Limited, London, England

[21] Appl. No.: 137,781

[22] Filed: Apr. 7, 1980

Related U.S. Application Data

[63] Continuation of Ser. No. 969,434, Dec. 14, 1978, abandoned.

[30] Foreign Application Priority Data

Dec. 20, 1977 [GB] United Kingdom ............... 52970/77

[51] Int. Cl.³ ...................... A01N 37/00; A01N 37/08
[52] U.S. Cl. ..................................... 424/305; 424/306
[58] Field of Search ................................ 424/305, 306

[56] References Cited

U.S. PATENT DOCUMENTS

3,996,375 12/1976 Frensch et al. ..................... 424/276
4,173,651 11/1979 Muramoto et al. ................. 424/306

FOREIGN PATENT DOCUMENTS

1209524 10/1970 United Kingdom .
1413491 11/1975 United Kingdom .
1569707  6/1980 United Kingdom .

OTHER PUBLICATIONS

Chemical Abstracts 84:131121x (1976).
Chemical Abstracts 87:97291c (1977).
Maas–"ULV Application and Formulation (pp. 61–71) Techniques", N.V. Philips-Duphar, Amsterdam, Neth. (1971).
Law et al.–Transactions of the ASAE, vol. 9, 1966, pp. 501–506.

*Primary Examiner*—Leonard Schenkman
*Attorney, Agent, or Firm*—Cushman, Darby & Cushman

[57] ABSTRACT

An electrostatically sprayable insecticidal formulation comprising a solution of from 0.5 to 50% of permethrin or like compound in an organic solvent medium, the medium being formulated so that the formulation has a resistivity at 20° C. in the range $1 \times 10^6$ to $1 \times 10^{10}$ ohm centimeter and a viscosity at 20° C. of 5 to 50 centistokes.

4 Claims, No Drawings

ELECTROSTATICALLY SPRAYABLE INSECTICIDAL FORMULATIONS

This is a continuation of application Ser. No. 969,434, filed Dec. 14, 1978, now abandoned.

This invention relates to insecticidal formulations, and more particularly to insecticidal formulations containing permethrin and like insecticides.

Permethrin is a recently discovered (U.K. Pat. No. 1413491 to the National Research Development Corporation) highly active insecticide of formula:

$$C_6H_5-O-\phantom{x}-CH_2-O-C(=O)-CH-CH-CH=CCl_2,\ \ C(CH_3)_2$$

It has a broad spectrum of activity at low rates of application, being particularly effective against lepidoptera, and seems likely to be widely used, for example against spruce budworm and pests of cotton. There is a group of related compounds with generally similar properties to permethrin having the general formula:

$$C_6H_5O-\phantom{x}-CH(R)-O-C(=O)-R^1$$

where R is hydrogen or cyano, and $R^1$ is either (i) a group of formula:

$$X-\phantom{x}-CH-CH(CH_3)_2$$

where X is hydrogen, chlorine or methyl; or (ii) a group of formula:

$$\begin{array}{c} Y \\ \phantom{x} \\ Z \end{array} C \begin{array}{c} CH- \\ \phantom{x} \\ C(CH_3)_2 \end{array}$$

where Y and Z are halogen or methyl or Y is hydrogen and Z is methyl or a group of formula:

$$\begin{array}{c} R^2 \\ \phantom{x} \\ R^3 \end{array} C=CH-$$

where $R^2$ and $R^3$ are chlorine or bromine. Additionally, at least one of $R^2$ and $R^3$ may be methyl or ethyl, optionally substituted by one or more halogen atoms. This group of insecticides is hereinafter referred to collectively as "permethrin and like compounds".

Permethrin and like compounds, being active at low rates, are well suited to agricultural application by the known ULV (ultra-low volume) technique. This method uses relatively concentrated liquid formulations, containing e.g. 5 to 50% by weight of active ingredient, and a correspondingly low rate of application of the formulation per hectare, e.g. 25–100 liters per hectare, in contrast with more usual high volume spray rates of 200–500 liters per hectare, or more. With such relatively concentrated solutions, it is important to ensure that as much as possible of the formulation goes and stays where it is needed, i.e. on the plants being sprayed, and as little as possible is misdirected onto the ground or carried away by the wind. For this purpose, it is useful to apply electrostatically charged sprays. These are attracted to the foliage of plants; electrostatic forces carry them to the underside of leaves as well as to the top surfaces, and even coating is promoted. Hitherto electrostatic spraying of pesticides has not been widely adopted, for lack of convenient, reliable and cheap spraying apparatus. A suitable apparatus is however now available, and is described in U.K. patent application No. 29539/76 (U.S. Ser. No. 812,440). We have also found that ultra-low volume sprays of permethrin and like compounds are biologically more effective in the form of small droplets e.g. below 70 u in diameter. Such droplets are particularly prone to drift unless electrostatically charged.

The object of the present invention is to provide a class of insecticidal compositions particularly suited to ULV electrostatic spraying, in particular by the apparatus described in U.K. patent application No. 29539/76 (U.S. Ser. No. 812,440).

According to the present invention we provide an electrostatically sprayable insecticidal formulation comprising a solution of from 0.5 to 50% of permethrin and like compounds (as herein defined) in an organic solvent medium, the formulation having a resistivity at 20° C. in the range $1 \times 10^6$ to $1 \times 10^{10}$ ohm centimeter and a viscosity at 20° C. of 1 to 50 centistokes. In general with higher resistivity values ($10^8$ to $10^{10}$ ohm centimeters), it is preferred to use higher viscosity values, e.g. above 10 centistokes. In this way, lower spray droplet sizes are obtainable.

We find that solutions according to the invention are readily sprayed at satisfactory rates using the apparatus of U.K. patent application No. 29539/76 (U.S. Ser. No. 812,440) and will give a range of mean spray droplet sizes of from about 50 to about 200 microns in diameter, according to the strength of the electrostatic field applied to them (the stronger the field the smaller the droplets), flow rate through the apparatus and other operating conditions.

The resistivity of solutions according to the invention is conveniently measured by measuring the resistance of a cell of standard dimensions containing the solution held at a temperature of 20° C., using, for example, a Keithley electrometer. It is preferred that the resistivity of the solutions be in the range $10^6$ to $5 \times 10^8$ ohm centimeters.

The viscosity of solutions according to the invention is conveniently measured by timing the flow of a measured quantity of the solution through a hole of known size (as is done, for example, in the Redwood viscometer). It is preferred that the viscosity of the solutions is in the range 5 to 25 centistokes.

The resistivity and viscosity of the solutions depend primarily on the properties of the solvents used to make them, though they are also affected by the nature and amount of the dissolved insecticide.

One way of obtaining the desired properties is to mix solvents having various resistivities and viscosities. High-boiling hydrocarbon solvents, e.g. 'Solvesso' 150, 'Isopar' L and 'Exsol' D180/220, are convenient and relatively cheap, but usually have low viscosities (e.g. of the order of 3 centistokes) and high resistivities (e.g. of the order of $10^{11}$ ohm centimeters). To bring down the resistivity of these materials, they may be mixed with polar solvents such as alcohols and in particular ketonic solvents. These have lower resistivities but are also usually not viscous enough; for example, the useful solvent cyclohexanone has a resistivity of about $2 \times 10^6$ ohm centimeters, but a viscosity of only about 3 centistokes. However the viscosity of the solution may be increased by addition of more viscous oil-soluble solvents, for example polybutenes e.g. 'Hyvis' (Trademark) and long-chain chlorinated hydrocarbon products such as 'Cerechlor' (Trademark) C42 or C48. The latter has a high resistivity, greater than $10^{10}$ ohm centimeters, and a high viscosity, of the order of 100 centistokes. By suitable adjustment of the proportions of three solvents such as these, a solution of the desired properties can easily be obtained.

The resistivity of solvents and solutions is easily affected by the presence of water or other contaminants. It is not necessary always to use ultra-pure materials, but consistent results will only be obtained from materials of consistent composition; and formulations which have been made up with the desired properties should thereafter be protected from any further contamination, especially by water.

An alternative way of producing a solution with the required properties is to make up a solution of the required viscosity but excessive resistivity (e.g. from a mixture of hydrocarbons and long-chain chlorinated hydrocarbons) and then dose this with an antistatic agent to reduce the resistivity to the desired level. A suitable antistatic agent is sold for use as a static charge dissipator with hydrocarbon fuels under the name 'ASA'; it consists of a complex mixture of calcium and chromium cations with various organic acid anions. Other similar materials, e.g. copper oleates, may also be used. This technique is not always suitable by itself for producing solutions having a resistivity below about $10^8$.

Examples of insecticides suitable for use in the solutions of the invention are listed below in Table I. In general, the presence of one or more asymmetric carbon atoms, as well as of a cyclopropane ring and (in some cases) a carbon-carbon double bond in these insecticides leads to the possibility of a number of different stereoisomers and geometrical isomers. The invention visualises using both pure isomers and mixtures of isomers, the former being potentially more active, the latter cheaper.

TABLE I

| COMPOUND NO | COMMON NAME | R | R[1] | X | Y | Z |
|---|---|---|---|---|---|---|
| 1 | permethrin | H | (ii) | — | H | $—CH{=}CCl_2$ |
| 2 | cypermethrin | CN | (ii) | — | H | $—CH{=}CCl_2$ |
| 3 | decamethrin | CN | (ii) | — | H | $—CH{=}CBr_2$ |
| 4 | | H | (i) | p-Cl | — | — |
| 5 | | H | (ii) | — | H | $—CH{=}C(CF_3)_2$ |
| 6 | | CN | (ii) | — | H | $—CH{=}C(CF_3)_2$ |
| 7 | | H | (ii) | — | H | $—CH{=}C(CF_3)Cl$ |
| 8 | | CN | (ii) | — | H | $—CH{=}C(CF_3)Cl$ |
| 9 | | H | (ii) | — | H | $—CH{=}C(CF_3)Br$ |
| 10 | | CN | (ii) | — | H | $—CH{=}C(CF_3)Br$ |
| 11 | phenothrin | H | (ii) | — | H | $—CH{=}C(CH_3)_2$ |

Preferably the concentration of active ingredient is not more than 10% by weight of the solution. If desired, the solutions of the invention may additionally contain quantities of other active ingredients dissolved therein.

The following Examples illustrate the invention.

EXAMPLE 1

The following solution was made by mixing together the constituents.

| Ingredient | Parts by Weight |
|---|---|
| Technical permethrin | 50 |
| "Solvesso" 150 | 350 |
| Cyclohexanone | 100 |
| "Cerechlor" C42 | 500 |

Viscosity 21.2 centistokes; resistivity $1.2\times10^8$ ohm centimeters (both measured at 20° C.).

This solution was tested in the device illustrated in FIGS. 1-3 of U.K. patent application No. 29539/76 (U.S. Ser. No. 812,440), and atomised very satisfactorily.

EXAMPLE 2

A formulation ("Formulation A") of permethrin was prepared suitable for ultra-low volume spraying. This had the following composition:

| Constituent | Parts by Weight |
|---|---|
| Permethrin | 50 |
| Cottonseed oil | 200 |
| "Isopar" L (trade name for a high-boiling paraffin fraction) | 750 |
| | 1000 |

Formulation A had a viscosity of 7.0 centistokes and a resistivity of $10^{11}$ ohm cm. Attempts to spray it through the device illustrated in FIGS. 1-3 of U.K. patent application No. 29539/76 were unsuccessful. The formulation was therefore modified to give a composition according to the invention, by mixing the following ingredients.

| Constituent | Parts by Weight |
|---|---|
| Formulation A | 700 |
| "Cerechlor" C48 | 290 |
| ASA-3 (antistatic additive) | 10 |
| | 1000 |

The modified composition had a viscosity of 19.5 centistokes and a resistivity of $2.4\times10^8$ ohm cm, and sprayed very satisfactorily through the aforesaid device.

EXAMPLE 3

The following solution was made by mixing together the constituents.

| Ingredient | Parts by Weight |
|---|---|
| Technical cypermethrin | 12.5 |
| n-butanol | 220 |
| 'Solvesso' 100 | 150 |
| Cottonseed oil | to 1000 |

Viscosity 11.0 centistokes; resistivity $5.4\times10^7$ ohm centimeters (both measured at 20°).

This solution atomised satisfactorily when tested as in Example 1.

EXAMPLE 4

The following solution is made by mixing together the constituents:

| Ingredient | Parts by Weight |
|---|---|
| Compound No. 8 of Table 1 (mixture of isomers) | 15 |
| n-butanol | 220 |
| 'Solvesso' 100 | 150 |
| Cottonseed oil | to 1000 |

Viscosity 11 centistokes; resistivity $5.4 \times 10^7$ ohm centimeters (both at 20° C.).

This solution atomises satisfactorily when tested as in Example 1.

EXAMPLES 5-11

Seven compositions according to the invention were prepared from cypermethrin (compound No. 2 of Table I) by mixing together the constituents. In each case the resulting solution atomised satisfactorily when tested as in Example 1. The cypermethrin used was a technical grade mixture of isomers supplied as a 34% solution in 'Aromasol' H hydrocarbon solvent. Viscosity data are given in centistokes and resistivities in ohm centimeters.

EXAMPLE 5

| Ingredient | Parts by Weight |
|---|---|
| Cypermethrin | 12.5 |
| 'Aromasol' H | 25 |
| n-butanol | 220 |
| 'Solvesso' 100 | 150 |
| Cottonseed oil | 592.5 |
| | 1000 |

Properties at 20° C.: Viscosity 11.0; Resistivity $5.4 \times 10^7$; Density 0.886.

EXAMPLE 6

| Ingredient | Parts by Weight |
|---|---|
| Cypermethrin | 12.5 |
| 'Aromasol' H | 25 |
| n-butanol | 220 |
| 'Isopar' L | 150 |
| Cottonseed oil | 592.5 |
| | 1000 |

Properties at 20° C.: Viscosity 12.4; Resistivity $6.0 \times 10^7$; Density 0.862.

EXAMPLE 7

| Ingredient | Parts by Weight |
|---|---|
| Cypermethrin | 12.5 |
| 'Aromasol' H | 25 |
| Cyclohexanone | 220 |
| 'Isopar' L | 150 |
| Cottonseed oil | 592.5 |
| | 1000 |

Properties at 20° C.: Viscosity 15; Resistivity $4.6 \times 10^7$; Density 0.896.

EXAMPLE 8

| Ingredient | Parts by Weight |
|---|---|
| Cypermethrin | 12.5 |
| 'Aromasol' H | 25 |
| 'Isopar' L | 150 |
| ASA 3 | 175 |
| Cottonseed oil | 637.5 |
| | 1000 |

Properties at 20° C.: Viscosity 50; Resistivity $4.7 \times 10^7$; Density 0.898.

EXAMPLE 9

| Ingredient | Parts by Weight |
|---|---|
| Cypermethrin | 12.5 |
| 'Aromasol' H | 25 |
| 'Exsol' D180/220 | 150 |
| ASA 3 | 175 |
| Cottonseed oil | 637.5 |
| | 1000 |

Properties at 20° C.: Viscosity 43; Resistivity $4.7 \times 10^7$; Density 0.898.

EXAMPLE 10

| Ingredient | Parts by Weight |
|---|---|
| Cypermethrin | 12.5 |
| 'Aromasol' H | 25 |
| Cyclohexanone | 220 |
| 'Isopar' L | 150 |
| Cottonseed oil | 592.5 |
| | 1000 |

Properties at 20° C.: Viscosity 7; Resistivity $5.0 \times 10^7$; Density 0.851.

EXAMPLE 11

| Ingredient | Parts by Weight |
|---|---|
| Cypermethrin | 12.5 |
| 'Aromasol' H | 25 |
| 'Hyvis' 30 | 100 |
| 'Isopar' L | 200 |
| White Oil | 447.5 |
| Cyclohexanone | 220 |
| | 1000 |

Properties at 20° C.: Viscosity 10; Resistivity $5.1 \times 10^7$; Density 0.856.

"Solvesso" 100 and 150 are mixtures of aromatic hydrocarbons with boiling point ranges of 164°-174° C. and 190°-208° C., respectively.

"Isopar" L is a mixture of isoparaffinic hydrocarbons with a boiling range of 189°-208° C.

"Exsol" D180/220 is a mixture of paraffinic hydrocarbons and cycloparaffinic hydrocarbons having a boiling point range of 182°-220° C.

"Aromasol" H is a mixture of aromatic hydrocarbons.

"Cereclor" C42 and C48 are mixtures of chlorinated long chain paraffinic hydrocarbons containing, respectively, 42% and 49% by weight of chlorine.

"Hyvis" 30 is a polybutene thickening agent.

We claim:

1. An electrostatically sprayable insecticidal formulation suitable for use in an electrostatic spraying apparatus to spray plants to give an even coating of the insecticide on the leaves of said plants, the formulation having after spraying a spray droplet size in the range of from about 50 to about 200 microns in diameter, and consisting essentially of a solution of from 0.5 to 50% by weight of an insecticide in an inert organic solvent medium, said medium being a mixture of inert organic solvents or a mixture of inert organic solvents and an antistatic agent, formulated so that the formulation has a resistivity at 20° C. in the range $1 \times 10^6$ to $1 \times 10^{10}$ ohm centimeters, and a viscosity at 20° C. in the range 5 to 50 centistokes, and the insecticide being of formula:

$$C_6H_5-C_6H_4-CH(R)-O-\underset{\underset{O}{\|}}{C}-R^1$$

where R is hydrogen, and $R^1$ is selected from the group consisting of:

(i) a group of formula:

$$X-C_6H_3(CH-CH(CH_3)_2)$$

where X is selected from hydrogen, chlorine and methyl, and (ii) a group of formula:

$$\begin{array}{c} Y \\ \diagdown \\ Z \diagup \end{array} C \begin{array}{c} CH- \\ \diagup \\ \diagdown C(CH_3)_2 \end{array}$$

where Y and Z are selected from halogen, methyl, and a group of formula $R^2R^3C=CH-$, where $R^2$ and $R^3$ are selected from chlorine, bromine, methyl, ethyl, halo-substituted methyl and halo-substituted ethyl.

2. A formulation as claimed in claim 1 having a viscosity at 20° C. in the range 5 to 25 centistokes.

3. An electrostatically sprayable insecticidal formulation as claimed in claim 1 consisting essentially of a solution of from 0.5 to 10% by weight of an insecticide selected from the group consisting of permethrin and cypermethrin in an organic solvent medium comprising from 15 to 25% of an alcoholic or ketonic solvent, from 10 to 20% by weight of a hydrocarbon solvent and from 55 to 65% by weight of cottonseed oil, the formulation having a viscosity at 20° C. in the range 5 to 50 centistokes and a resistivity at 20° C. in the range $10^6$ to $5 \times 10^8$ ohm centimeters.

4. A method of treating a plant infested by insects, said method consisting essentially of the step of electrostatically spraying the plant with an insecticidally effective amount of a formulation as claimed in claim 1 so as to provide an even coating of the insecticide on the leaves of said plant.

* * * * *